(12) United States Patent
Wyland

(10) Patent No.: US 12,310,841 B2
(45) Date of Patent: May 27, 2025

(54) FIBROUS CONNECTIVE TISSUE PROTECTIVE DEVICE, METHOD OF MANUFACTURING, AND SURGICAL METHOD

(71) Applicant: Zimmer, Inc., Warsaw, IN (US)

(72) Inventor: Douglas J. Wyland, Greer, SC (US)

(73) Assignee: Zimmer, Inc., Warsaw, IN (US)

( * ) Notice: Subject to any disclaimer, the term of this patent is extended or adjusted under 35 U.S.C. 154(b) by 686 days.

(21) Appl. No.: 17/437,546

(22) PCT Filed: Mar. 20, 2020

(86) PCT No.: PCT/US2020/023778
§ 371 (c)(1),
(2) Date: Sep. 9, 2021

(87) PCT Pub. No.: WO2020/197973
PCT Pub. Date: Oct. 1, 2020

(65) Prior Publication Data
US 2022/0151764 A1 May 19, 2022

Related U.S. Application Data

(60) Provisional application No. 62/959,455, filed on Jan. 10, 2020, provisional application No. 62/822,265, filed on Mar. 22, 2019.

(51) Int. Cl.
*A61F 2/08* (2006.01)
(52) U.S. Cl.
CPC ..... *A61F 2/0811* (2013.01); *A61F 2002/0858* (2013.01); *A61F 2002/0888* (2013.01)

(58) Field of Classification Search
CPC ............ A61F 2/0811; A61F 2002/0858; A61F 2002/0888; A61F 2002/0823; A61F 2002/0835; A61F 2210/0076; A61F 2220/0008; A61F 2250/001; A61F 2250/0017; A61F 2250/0023; A61F 2250/0028; A61F 2250/0039
See application file for complete search history.

(56) References Cited

U.S. PATENT DOCUMENTS 4,795,466 A * 1/1989 Stuhmer .................. D03D 1/00
87/9
5,139,520 A 8/1992 Rosenberg
(Continued)

FOREIGN PATENT DOCUMENTS

WO 2015/009246 1/2015
WO WO-2017030928 A1 * 2/2017 ......... A61B 17/0401
WO 2020197973 10/2020

OTHER PUBLICATIONS

"International Application Serial No. PCT US2020 023778, International Preliminary Report on Patentability mailed Oct. 7, 2021", 14 pgs.
(Continued)

*Primary Examiner* — Paul B Prebilic
(74) *Attorney, Agent, or Firm* — SCHWEGMAN LUNDBERG & WOESSNER, P.A.

(57) ABSTRACT

A device, a method of manufacturing, and a surgical method are disclosed in which fibrous connective tissues to be attached to bone are protected by a sleeve. An introducer may be used to assist in placing the fibrous connective tissue into the sleeve.

20 Claims, 16 Drawing Sheets

(56) References Cited

U.S. PATENT DOCUMENTS

| | | | |
|---|---|---|---|
| 5,456,721 A | 10/1995 | Legrand | |
| 5,984,926 A | 11/1999 | Jones | |
| 6,203,572 B1* | 3/2001 | Johnson | A61F 2/08 606/108 |
| 6,746,483 B1 | 6/2004 | Bojarski et al. | |
| 7,729,008 B2 | 6/2010 | Holub | |
| 8,663,324 B2 | 3/2014 | Schmieding et al. | |
| 8,834,521 B2 | 9/2014 | Pinto et al. | |
| 8,956,394 B1 | 2/2015 | McDonnell | |
| 9,801,707 B2* | 10/2017 | Cassani | A61F 2/0811 |
| 2012/0179253 A1* | 7/2012 | Altman | A61F 2/08 28/100 |
| 2017/0281327 A1 | 10/2017 | Kaplan et al. | |
| 2018/0228596 A1 | 8/2018 | Wyland | |

OTHER PUBLICATIONS

International Search Report and Written Opinion for International Application No. PCT/US2020/023778, dated May 27, 2020.
International Search Report on Patentability for Application No. PCT/US2016/046689, dated Feb. 20, 2018.

\* cited by examiner

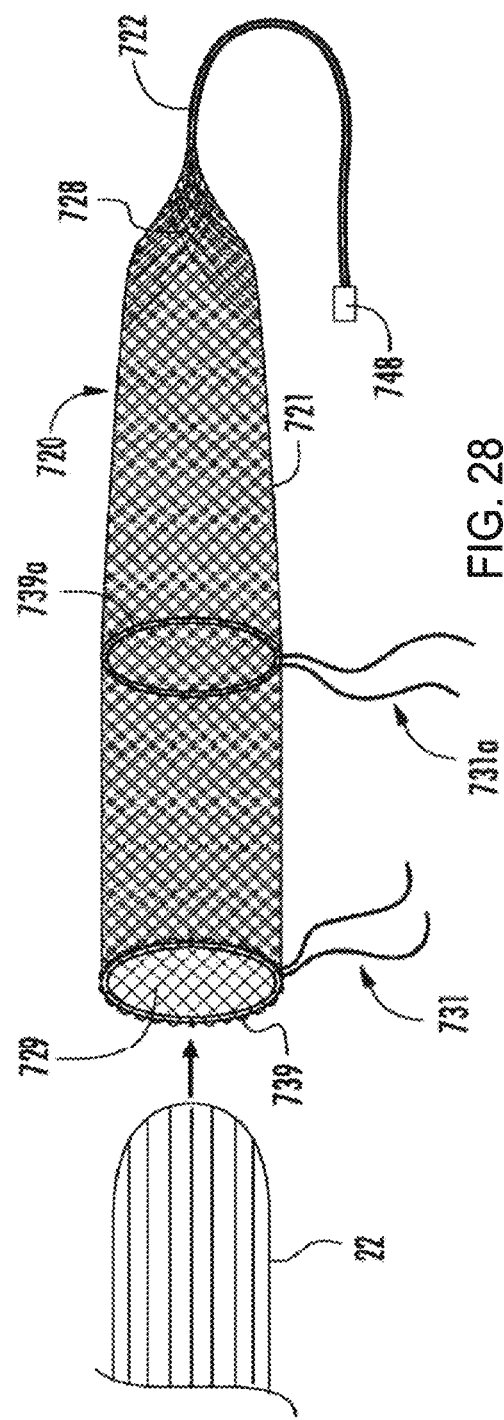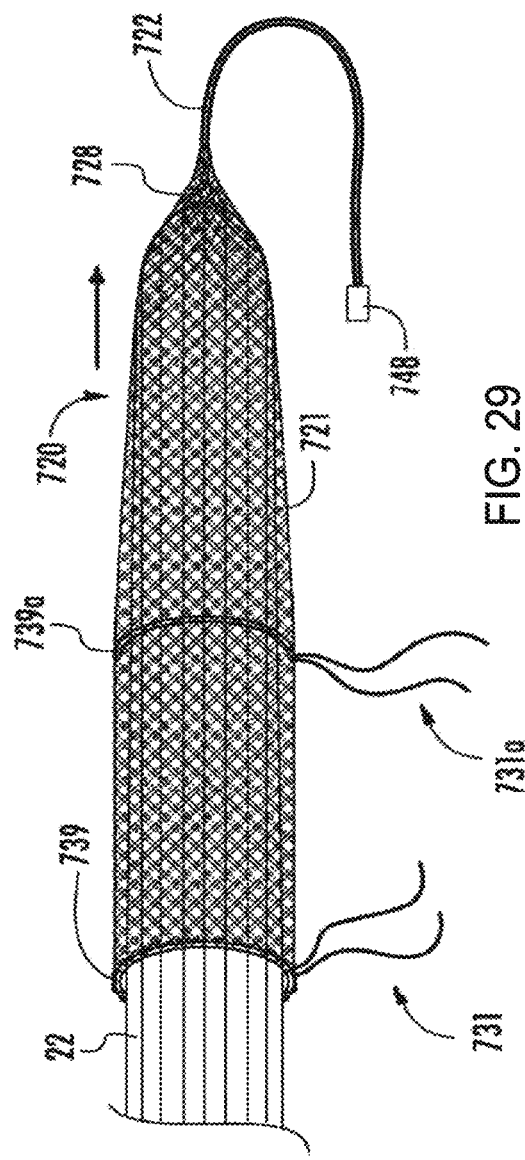

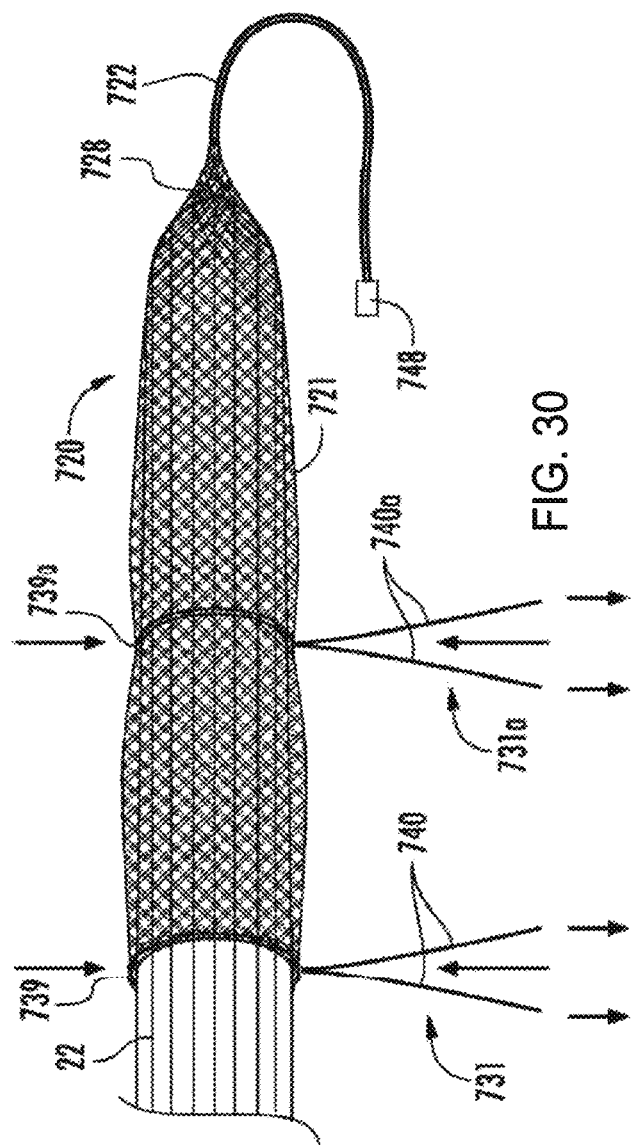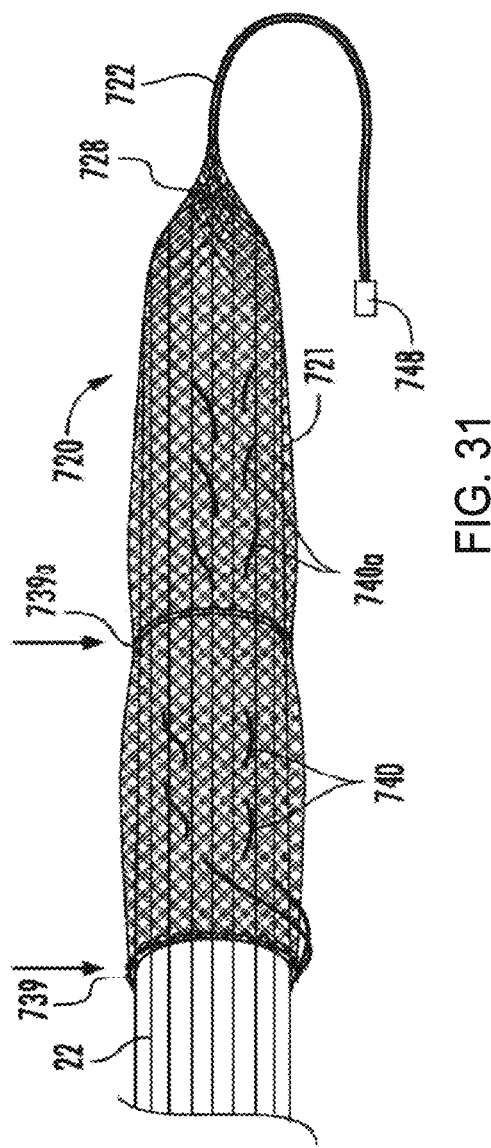

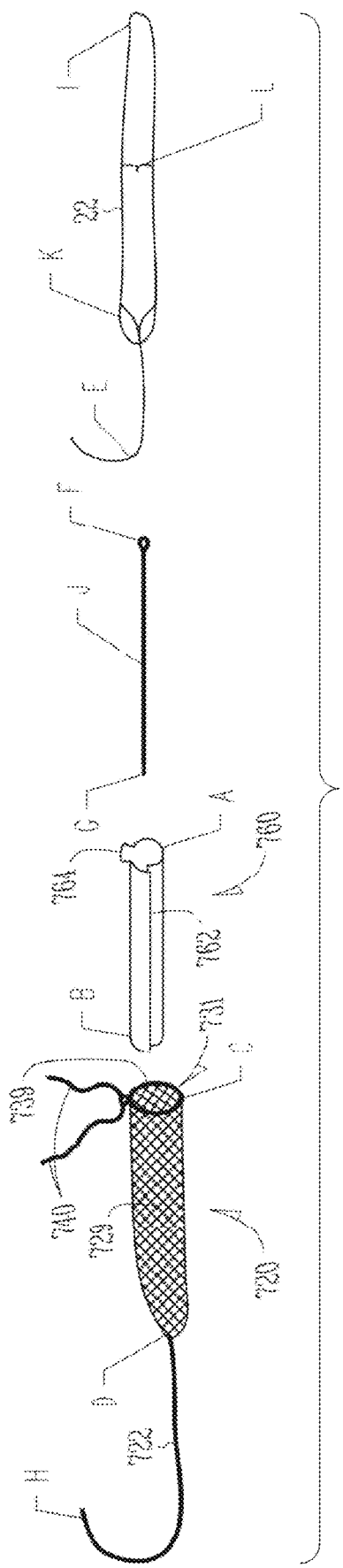
FIG. 32
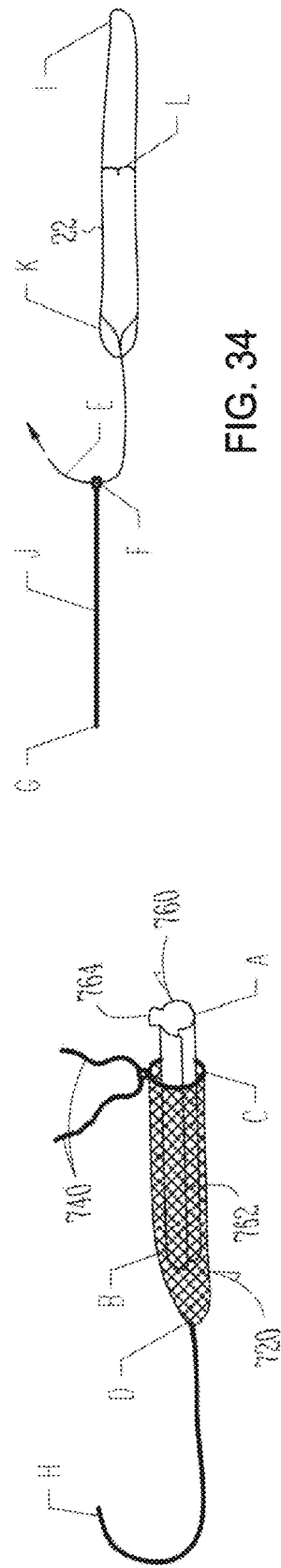
FIG. 33
FIG. 34

FIBROUS CONNECTIVE TISSUE PROTECTIVE DEVICE, METHOD OF MANUFACTURING, AND SURGICAL METHOD

CROSS-REFERENCE TO RELATED APPLICATIONS

This application is a national stage of International Application No. PCT/US2020/023778, filed Mar. 20, 2020, and claims benefit to U.S. Provisional Patent Application No. 62/822,265, filed Mar. 22, 2019, and 62/959,455, filed Jan. 10, 2020, all of which are incorporated by reference herein.

TECHNICAL FIELD

The present disclosure relates generally to a device, a manufacturing method, and a surgical method in which fibrous connective tissue to be attached to bone is protected by a sleeve, and an introducer is used to assist in placing the tissue in the sleeve.

BACKGROUND

Fibrous connective tissue grafts are used in numerous types of surgical procedures. Anterior cruciate ligament (ACL) and posterior cruciate ligament (PCL) replacement surgeries are but two examples. In such surgeries, patient or donor harvested grafts, or artificial tissue grafts, are attached between the tibia and femur. The grafts may be attached to passages such as sockets or tunnels formed in the tibia and femur. Securing members such as screws or button connectors may be employed to hold the graft in place. U.S. Pat. Nos. 5,139,520 and 8,663,324, for example, describe numerous ACL replacement concepts. The Bio-Tenodesis Screw System, available from Arthrex, Inc., includes a screw and a specialized driver tool for securing grafts in bone sockets. Other soft tissue surgeries are performed on muscles, tendons and ligaments such as the rotator cuff, Achilles tendon, patellar tendon, hips, elbows, shoulders, hands, etc., as noted for example in U.S. Pat. No. 8,834,521.

In surgeries in which graft material is connected to bone, a graft-bone interface area is formed. Depending on the particular surgery, the graft may be held in a passage by a securement device such as a screw or button, and may extend roughly normal to, perpendicular to, or at an intermediate angle to the bone surface. The graft may experience higher forces particularly adjacent the outer edge of the passage (e.g., along the bone cortex later), but also along the entire bone, securement device, and graft interface area.

Certain types of reinforcements have been used in the interface area, both to assist in the secure seating of the screw/button and graft in the passage and to strengthen the graft in this area. For example, a surgeon preparing a graft may add whipstitching along the distal end of the graft for such purposes. The whipstitching may also be employed to add one or more extending sutures to the graft so that the graft can be pulled into and through passage in the bone to properly locate the graft. Adding whipstitching, while conventional and effective, is an extra step during surgery that requires due care and an amount of extra time, tools and material.

Woven elements, such as are shown for example in U.S. Pat. Nos. 8,956,394, 7,729,008, and 6,203,572, have been disclosed for use in surgeries. As noted in these patents, the elements may be used with a screw or graft during the surgery to assist with the location, manipulation or securement of the various elements. However, a need still exists for an improved protective device for a distal end of a fibrous connective tissue that efficiently and effectively avoids certain drawbacks of existing devices and their related surgical methods, and/or provides certain other benefits to the surgeon and patient, such as protection of the distal end and fostering tissue growth after surgery.

SUMMARY

According to certain aspects of the disclosure, a protective device is disclosed for a fibrous connective tissue to be secured within a passage in a bone by a securing device, the protective device including, for example, a sleeve woven from a plurality of strands. The sleeve has a double-tubular structure and a suture portion, the double-tubular structure having an inner tubular structure and an outer tubular structure circumferentially surrounding the inner tubular structure. The strands extend from respective first ends through the suture portion, through the inner tubular structure, reverse direction at a circumferential reversing bend, through the outer tubular structure, and through the suture portion to respective second ends. An opening is defined at the circumferential reversing bend, and a passage extends from the opening toward the suture portion within the double-tubular structure, the opening and passage being sized for receipt and securement of the fibrous connective tissue therein. A tightening member is located along the sleeve proximate the circumferential reversing bend. The tightening member includes a loop movable between a first loosened position in which the loop is sized sufficiently to permit movement of the fibrous connective tissue therethrough into the passage and a second tightened position in which the loop is reduced in size sufficiently to assist in securing the fibrous connective tissue in place in the passage. Various options and modifications are possible.

For example, the loop may be woven into the double-tubular structure, the loop may be located between the inner tubular structure and the outer tubular structure, the tightening member may further include at least one strand extending from the loop through the outer tubular structure, and/or the tightening member may include external frictional structure for resisting movement from the second tightened position toward the first loosened position. At least one additional tightening member may be provided spaced from the tightening member in a direction along the double-tubular structure toward the suture portion, and the at least one additional tightening member may be configured to be substantially similar to the tightening member.

The double-tubular structure may have a strand weave density sufficient to allow tissue growth between the strands after securement in the bone, the strand weave density may vary between the circumferential reversing bend and the suture portion, the strand weave density may be higher in a neck-down portion adjacent the suture portion than along other portions of the double-tubular structure, and/or the inner tubular structure may define an inner diameter along the passage, the inner diameter decreasing in the neck-down portion in a direction toward the suture portion.

The double-tubular portion may be configured to move from a rest position to a self-lockingly tightened position when the fibrous connective tissue is inserted into the passage and the double-tubular structure is stretched in a direction along the passage, and/or at least a portion of the strands may have an external frictional structure for resisting movement from the self-lockingly tightened position toward the rest position.

The sleeve may include at least one of a non-bioabsorbable material, a bioabsorbable material, a biologic material (which may include one or more of a collagen matrix, a stem cell and a platelet rich plasma).

The sleeve may be sized for use in a tendon surgery and the fibrous connective tissue would be a tendon. The sleeve may be sized for use in a ligament surgery and the fibrous connective tissue would be a ligament. The passage may have a diameter that decreases in the direction of the second end.

According to certain other aspects of the disclosure, a surgical method is disclosed for securing a fibrous connective tissue having a distal end portion within a passage in a bone, the surgical method including, for example: inserting the distal end portion of the fibrous connective tissue into a passage within a protective device having: (a) a sleeve woven from a plurality of strands, the sleeve having a double-tubular structure and a suture portion, the double-tubular structure having an inner tubular structure and an outer tubular structure circumferentially surrounding the inner tubular structure, the strands extending from respective first ends through the suture portion, through the inner tubular structure, reversing direction at a circumferential reversing bend, through the outer tubular structure, and through the suture portion to respective second ends, an opening defined at the circumferential reversing bend and a passage extending from the opening toward the suture portion within the double-tubular structure, the opening and passage being sized for receipt and securement of the fibrous connective tissue therein; and (b) a tightening member located along the sleeve proximate the circumferential reversing bend, the tightening member including a loop movable between a first loosened position in which the loop is sized sufficiently to permit movement of the fibrous connective tissue therethrough into the passage and a second tightened position in which the loop is reduced in size sufficiently to assist in securing the fibrous connective tissue in place in the passage; the method further including placing the distal end portion into the passage into the sleeve; securing the fibrous connective tissue within the passage in the sleeve at least partially by tightening the loop; inserting the fibrous connective tissue and protective device at least partially into the passage in the bone; and securing the fibrous connective tissue and protective device to the passage in the bone. Various options and modifications are possible.

For example, the step of securing the fibrous connective tissue within the passage may include self-lockingly tightening strands of the sleeve around the fibrous connective tissue, and the step of securing the fibrous connective tissue within the passage may further include stitching the sleeve to the fibrous connective tissue. The method may also further include tightening a loop of at least one additional tightening member spaced from the tightening member in a direction along the sleeve toward the suture portion. The loop may be woven into the double-tubular structure, the loop may be located between the inner tubular structure and the outer tubular structure, the tightening member may further include at least one strand extending from the loop through the outer tubular structure, and/or the tightening member may further include external frictional structure for resisting movement from the second tightened position toward the first loosened position.

The securing the fibrous connective tissue and protective device to the passage in the bone step may include placing a screw into the passage in the bone, and/or attaching a button fastener through the passage in the bone. The passage in the bone may be one of a socket or a tunnel. The fibrous connective tissue may be at least one of a tendon, a ligament, an autograft, an allograft, a heterograft, or an artificial tissue. The method may include intra-articular surgery, extra-articular surgery, or tenodesis surgery According to another aspect of the disclosure, a method is disclosed for manufacturing a protective device configured for securing a fibrous connective tissue therein for use during surgery, the method including, for example: forming a sleeve having a double-tubular structure from a plurality of plurality of strands by weaving from respective first ends, through a suture section, through an inner tubular structure, reversing at a circumferential reversing bend, through an outer tubular structure, through the suture portion to respective second ends, an opening defined at the circumferential reversing bend and a passage extending from the opening toward the suture portion within the double-tubular structure, the opening and passage being sized for receipt and securement of the fibrous connective tissue therein; and placing a tightening member along the sleeve proximate the circumferential reversing bend, the tightening member including a loop movable between a first loosened position in which the loop is sized sufficiently to permit movement of the fibrous connective tissue therethrough into the passage and a second tightened position in which the loop is reduced in size sufficiently to assist in securing the fibrous connective tissue in place in the passage. Various options and modifications are possible.

For example, the method may further include weaving at least one additional tightening member spaced from the tightening member in a direction along the sleeve toward the suture portion and/or securing together the first and the second sends of the strands to form a suture portion end. The placing step may include weaving the loop into the double-tubular structure, the loop being woven between the inner tubular structure and the outer tubular structure. The tightening member may further include at least one strand extending from the loop through the outer tubular structure.

The double-tubular structure may have a strand weave density sufficient to allow tissue growth between the strands after securement in the bone, the double-tubular structure may be woven with a strand weave density which varies between the circumferential reversing bend and the suture portion, the strand weave density may be higher in a neck-down portion adjacent the suture portion than along other portions of the double-tubular structure, and/or the inner tubular structure may define an inner diameter along the passage, the inner diameter decreasing in the neck-down portion in a direction toward the suture portion.

BRIEF DESCRIPTION OF THE DRAWINGS

More details of the present disclosure are set forth in the drawings.

FIGS. 28-31 are perspective diagrammatic views showing sequential steps of a surgical method using the protective device of FIG. 19 with fibrous connective tissue.

FIG. 32 is a perspective view of an alternate embodiment of a protective device and related kit, including an introducer.

FIGS. 33-40 are perspective diagrammatic views showing sequential steps of a surgical method using the device and kit of FIGS. 32.

DETAILED DESCRIPTION

Figure 1:
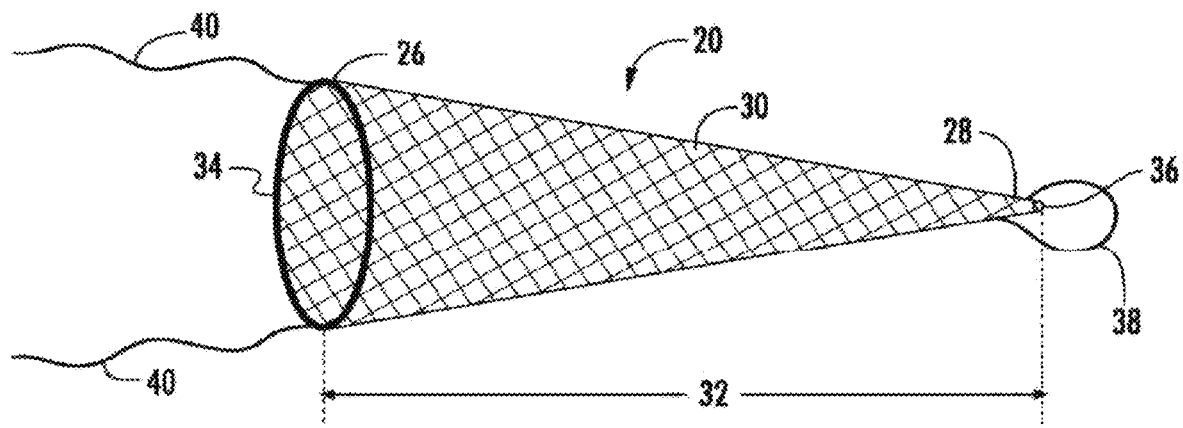
FIG. 1 is a perspective view of one example of a protective device according to certain aspects of the disclosure.

Detailed reference will now be made to the drawings in which examples embodying the present disclosure are shown. The detailed description uses numeral and letter designations to refer to features in the drawings. Like or similar designations in the drawings and description have been used to refer to like or similar parts of the disclosure.

The drawings and detailed description provide a full and enabling description of the disclosure and the manner and process of making and using it. Each embodiment is provided by way of explanation of the subject matter not limitation thereof. In fact, it will be apparent to those skilled in the art that various modifications and variations may be made to the disclosed subject matter without departing from the scope or spirit of the disclosure. For instance, features illustrated or described as part of one embodiment may be used with another embodiment to yield a still further embodiment.

Generally speaking, FIGS. 1-40 show examples of different constructs, kits, manufacturing steps, and surgical steps for a protective device that can be used for securing fibrous connective tissue to a passageway in a bone. It should be understood that the fibrous connective tissues may be any such tissue suitable for surgical repair now or in the future, such as ligaments, tendons, etc. The fibrous connective tissues may be made of any sort suitable substance, such as an autograft, allograft, heterograft, or artificial tissue, etc. The fibrous connective tissues may be formed in many ways, including single strand, multiple strands, folded strands, linear or branched constructs, stitched, unstitched, etc.

Also, the bone may be any bone suitable for surgical connective fibrous tissue repair, such as a tibia, femur, or humerus, but also any other bone within the body. The surgical procedure may for example be intra-articular, extra-articular or tenodesis procedures. The passages formed in the bone may be in the form of a conventional socket, tunnel, or the like. The fibrous connective tissues may be attached to the passages in the bones with securement devices such as conventional screws, screws with swivel lock anchors, button devices, etc. The surgical procedures and locations are not limited to the human body and may include use with animal species.

Thus, it should be understood that the protective devices, kits, and surgical procedures disclosed herein have applicability beyond the examples disclosed below.

Figure 2:
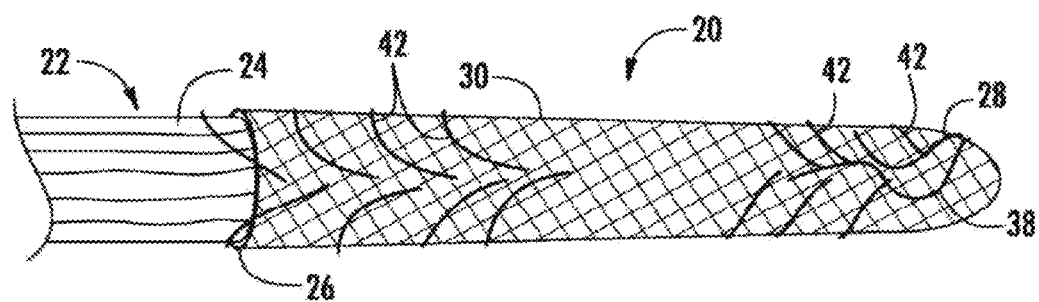
FIG. 2 is a perspective view of the protective device of FIG. 1 as secured to the distal end of a fibrous connective tissue.

More particularly, FIGS. 1-2 show an example of a protective device in the form of a sleeve 20 for use with a fibrous connective tissue 22 having a distal end portion 24. Sleeve 20 has a first end 26, a second end 28, and a tubular portion 30 of length 32 between the first and second ends. First end 26 defines an opening 34 sized for receiving distal end portion 24 of fibrous connective tissue 22 into the sleeve. Second end 28 defines an opening 36 sized for receiving a tool (see FIG. 7) for holding distal end portion 24 when fibrous connective tissue 22 is placed within the sleeve 20. It should be understood, however, that opening 36 is not required in all facets of the disclosure. Sleeve 20 is preferably configured so that length 32 of the sleeve 20 will cover and therefore protect the portion of fibrous connective tissue 22 within the sleeve while and after the tissue is secured in a bone passage, such as a socket or tunnel, as described below.

Sleeve 20 is formed of a woven material. Sleeve 20 is flexible and pliable so that it can be manipulated, stretched, tightened, etc., as needed during a procedure. The woven material may have a thread weave density sufficient to allow tissue growth between strands after securement in the bone. Sleeve 20 can be formed of various materials, either non-bioabsorbable and bioabsorbable, or combinations of both. Thus, different types and sizes of strands can be woven into sleeve 20 to provide different properties. The woven material can also be coated by or infused with a biologic material suitable for various purposes, such as one or more of a collagen matrix, a stem cell and a platelet rich plasma.

As shown in FIG. 1, sleeve 20 has a diameter that decreases in the direction of second end 28. FIG. 1 shows the decreasing diameter as a somewhat constant taper. However, other shapes are possible, as mentioned below.

An eyelet 38 may be included at second end 28. Eyelet 38 may be formed of threads that are woven into sleeve 20. Other threads 40 woven into sleeve 20 may extend from first end 26. Alternately, threads 40 and eyelet 38 may be formed of the same threads.

Sleeve 20 may be configured to tighten around fibrous connective tissue 22 when the sleeve is extended in a direction along the fibrous connective tissue. Thus, pulling longitudinally on sleeve 20 tightens and thins its weave, in some ways like a finger trap. In particular, pulling on threads 40 and/or eyelet 38 while holding sleeve 20 on fibrous connective tissue distal end portion 24 provides a locking attachment of the sleeve to the tissue. Sleeve 20 can be described as "self-locking" if after pulling on one or both of the threads 40 the sleeve 20 substantially retains its shape and grip on tissue 22. Depending on the surgeon's preference, such locking attachment may be used to hold sleeve 20 on tissue 22 until a screw is used to attach the sleeve and tissue to the bone. If desired, after threads 40 are pulled, the threads can be threaded back into the mesh of sleeve 20, tied as a secondary lock, or used as sutures (e.g., as a whipstitch) to further secure the sleeve to tissue 22.

Additional sutures 42, such as one or more stitches, whipstitching or other patterns, may also be used if it's the surgeon's preference to further secure sleeve 20 to the fibrous connective tissue once the sleeve is secured by the initial tightening (see FIG. 2). Sutures 42 may be formed from threads 40, or may be in addition to threads 40, and may be used to secure both ends 26, 28 of sleeve 20 to tissue 22. Such sutures 42 may also secure eyelet 38 to sleeve 20 after placement of sleeve on tissue 22 (as shown in FIG. 2), or eyelet 38 may be left to extend from sleeve (as shown in FIG. 1).

Figure 3:
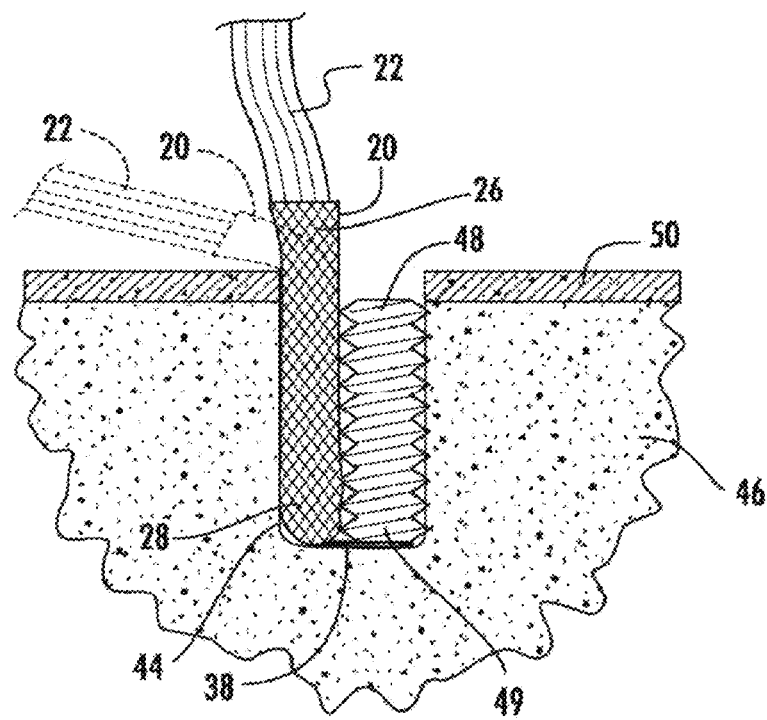
FIG. 3 is a diagrammatic sectional view of the protective device and fibrous connective tissue as in FIG. 2, as secured in a passage of a bone via a screw.

FIGS. 3-6 generally show examples of securement of a fibrous connective tissue graft to a passage in a bone using a securing device and a sleeve. FIG. 3 shows such an arrangement of distal end portion 24 of tissue 22, within sleeve 20, secured in a passage 44 in a bone 46 via a screw 48. As shown, passage 44 is a socket formed normally to the bone surface (outer cortex portion 50). Sleeve 20 extends out of passage just past outer cortex portion 50. Sleeve 20 therefore protects the graft during insertion of screw 48, during any surgical repositioning, and afterwards. In particular, sleeve 20 protects the interface between the edge of passage 44 along the cortex portion 50. As ligaments and tendons naturally exist to allow relative movement, they are subjected to various forces as a patient moves. Protection of the interface may be important, because a somewhat sharp edge may exist, and because forces may be transmitted at a sharp angle (see dotted line orientation in FIG. 3).

However, in the examples herein, the entire fibrous connective tissue graft 22 is not covered by sleeve 20. Central portions of the graft (between bone securement sites) would not necessarily need protection and reinforcement from bone and bone edge contact. Also, by only covering ends of the graft with sleeves, less material is used leading to a less bulky construct, which may be more convenient for handling during surgery, in particular arthroscopic surgery. Also, more options are available as to sizing by only covering ends; sleeves of different sizes may be used on different ends, and a family of differently sized sleeves may be provided for selection by the surgeon as needed.

By way of example, if passage 44 were a socket with a depth of 25 mm, sleeve 20 could have a longer length, e.g., 30 or 35 mm, so as to extend past cortex portion 50 along the outer surface of bone 46. Other dimensions and rations of such dimensions are possible, depending on the surgical site, surgeon preference, etc.

Also, the length and during- and post-surgical orientation of tissue 22, sleeve 20, and screw 48 may vary, which may also have an effect on the length of sleeve vs. depth of passage ratio. Thus, as shown in FIG.3, no portion of tissue 22 or sleeve is located along a bottom end 49 of screw 48. If end 28 of sleeve 20 on tissue 22 were to be held beneath bottom end 49 of screw 48 (rather than being located adjacent bottom end 49 of screw 48), then the sleeve used could be longer (relative to the depth of passage 44) so that end 26 of sleeve 20 still extends past cortex portion 50. Thus, and extra 5 or 10 mm of length could be added to sleeve 20 if it is to be inserted in such fashion, as compared to the dimensions set forth above.

If a tool with a gripping end portion, hook, loop, etc., is employed to insert screw 48, then such gripping element can engage eyelet 38. By doing so, the tissue 22 and sleeve 20 can be pulled into passage 44 in a desired orientation (either linearly as shown in FIG. 3 or with end 28 of sleeve 20 and tissue 22 beneath end 49 of screw 48, as described above). Such engagement of eyelet 28 can occur whether or not eyelet 38 has been stitched to sleeve/tissue as shown in FIG. 2. If a tool such as The Bio-Tenodesis System is employed, the distal end of the tool can contact and pull eyelet 38 and/or stitching 42 to place tissue 22 and sleeve 20 in passageway 44 before screw 48 is driven into place.

Figure 4:
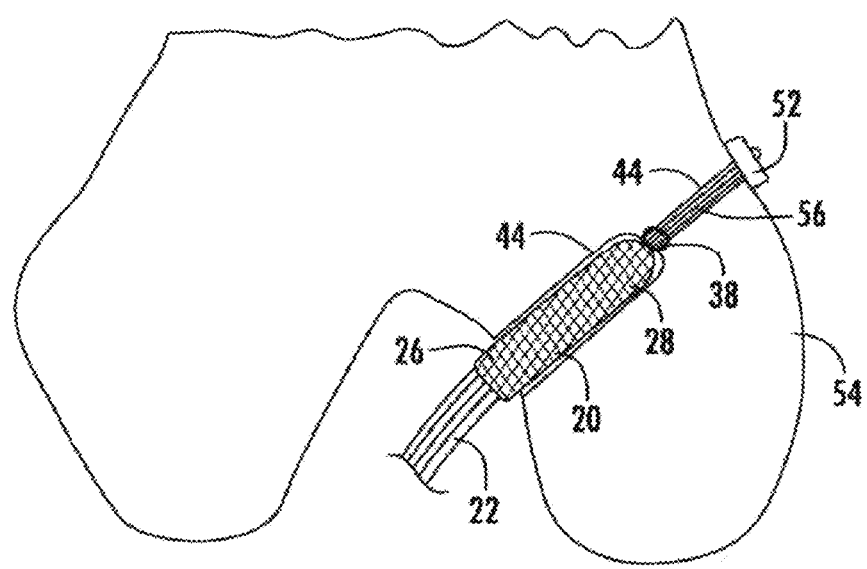
FIG. 4 is a diagrammatic view of the protective device and fibrous connective tissue as in FIG. 2, as secured in a passage of a bone via a button.

FIG. 4 shows sleeve 20 and fibrous connective tissue 22 connected to a tunnel-type passage extending through a bone such as a femur 54 by a conventional button fastener 52 and strands 56 attached to the sleeve and tissue construct. Sleeve 20 convers distal end portion 24 and extends just past the surface of bone 52, as above. Distal end portion 24 and sleeve 20 are connected to strands 56 by conventional stitching (not shown for clarity). A screw (not shown) can be used to further secure the sleeve and tissue in the tunnel.

Figure 5:
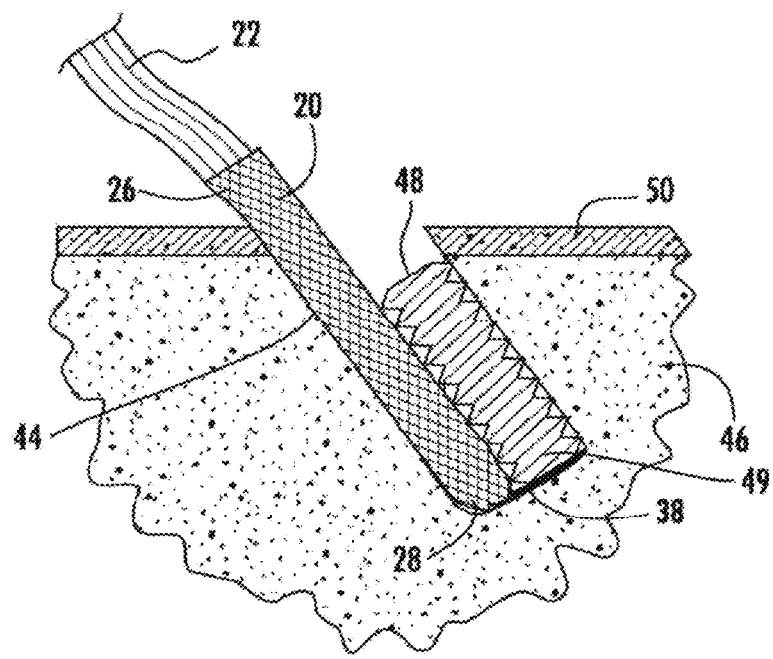
FIG. 5 is a diagrammatic sectional view of the protective device and fibrous connective tissue as in FIG. 2, as secured in a passage of a bone via a screw at an angle different than in FIG. 2.

FIG. 5 shows a screw-secured arrangement as in FIG. 3, but where passage 44 is a socket drilled in bone 46 at an angle to cortex portion 50.

Figure 6:
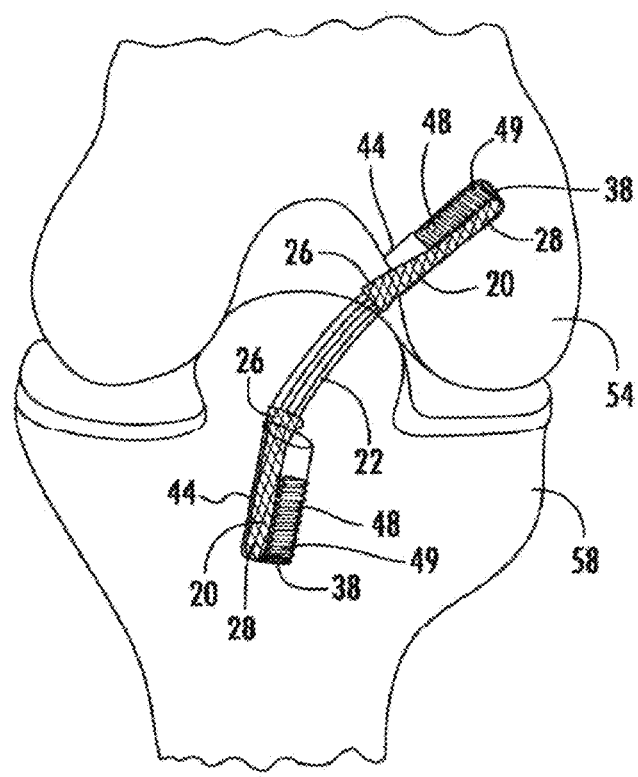
FIG. 6 is a diagrammatic view of two of the protective devices and a fibrous connective tissue as in FIG. 2, as secured in a knee joint via two screws.

FIG. 6 shows a knee joint including a femur 54 and tibia 58, in which a fibrous connective tissue 22 has been secured in two sockets 44 by screws 48. Sleeves 20 are located at each end of tissue 22, and extend just past the respective edges of the sockets 44, as above.

It should be understood that the above examples of tissue and bone are exemplary and non-limiting.

FIGS. 7-12 show one method of placement of a sleeve on a tissue, using a tool. As illustrated, tool 60 includes two gripping arms 62 attached to a central portion 64, one or both of which may be relatively movable toward and away from the other, generally in the form of a forceps, clamp, etc. The handle and operating mechanism of tool 60 need not be shown for purposes of this disclosure and could have many known forms.

Figure 7:
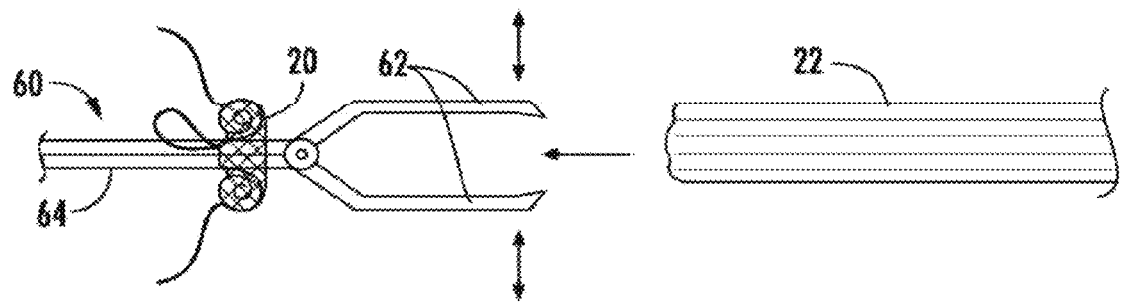
FIGS. 7-12 are perspective diagrammatic views showing one set of steps of a surgical method using the protective device and fibrous connective tissue as in FIG. 2.
Figure 8:
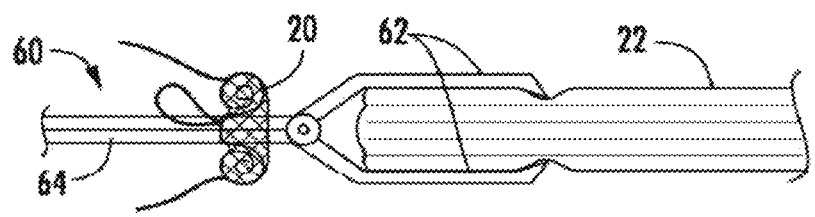

In FIG. 7, tool 60 is supplied with sleeve 20 placed over tool 60 in a rolled configuration so that central portion 64 extends through opening 36. Alternately, sleeve 20 can be slid onto tool 60 without rolling. Sleeve 20 is rolled into a small configuration and exposes gripping members 62 sufficiently that they can grip tissue 22. Gripping members 62 are opened, if necessary, to receive tissue 22 then closed to lightly clamp tissue 22, as shown in FIG. 8.

Figure 9:
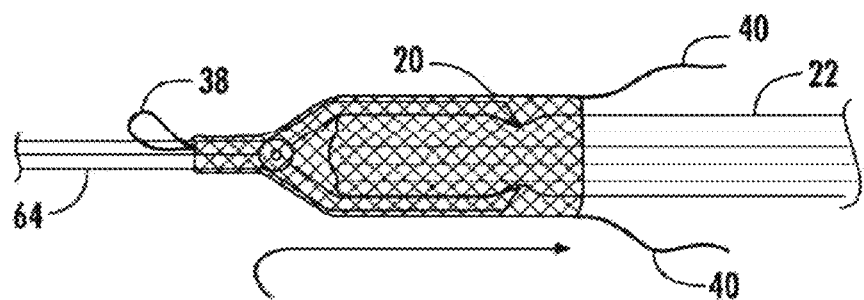

In FIG. 9, sleeve 20 has been unrolled to cover part of tissue 22 and more of tool 60. Note eyelet 38 and threads 40 (if present) would be exposed after unrolling.

Figure 10:
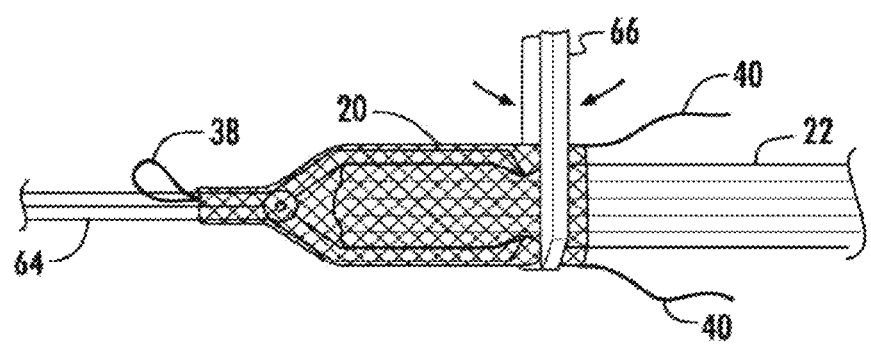

In FIG. 10, optionally a hemostat clamp 66 or the like may be employed to hold sleeve 20 on tissue 22 so that tool 60 can be removed. Accordingly, gripping members 62 release the tissue 22 at this point.

Figure 11:
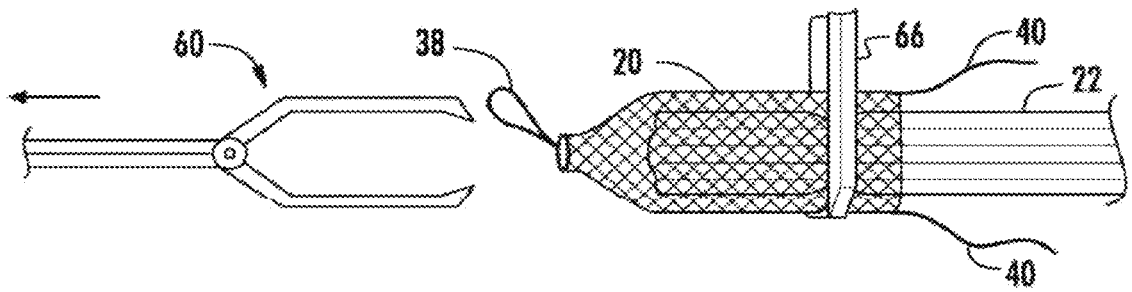

In FIG. 11, tool 60 has been slid out of sleeve 20 via opening 36. Note that the flexibility of the weave allows the tool to move out of sleeve 20 without damaging the sleeve.

Figure 12:
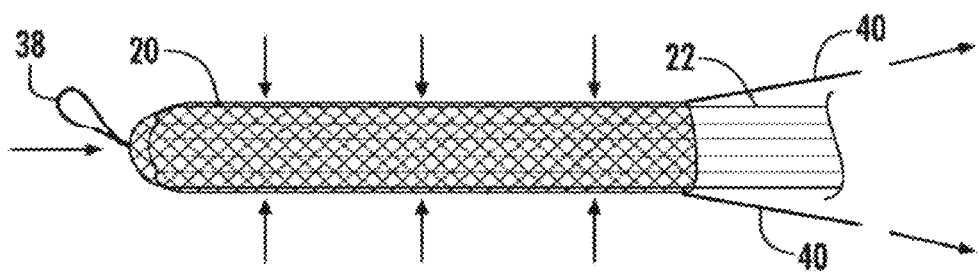

In FIG. 12, clamp 66 has been removed, and threads 40 have been pulled to lengthen sleeve 20 and tighten it around tissue 22. If desired, a clamp could be used in this step adjacent second end 36 while pulling on threads 40. If desired, eyelet 38 can use used to hold the second end, either directly or with a tool, during such pulling. The pulling of the woven sleeve tightens and preliminarily locks (and/or self-locks) it on distal end portion 24 of tissue 22. Suturing can then be added as desired to hold sleeve 20 to tissue 22, for example, to engage with bone screws, to assist in mounting a button securing structure, as shown in FIG. 2. Eyelet 38 can be employed as some or part of the button mounting structure, if desired.

Figure 13:
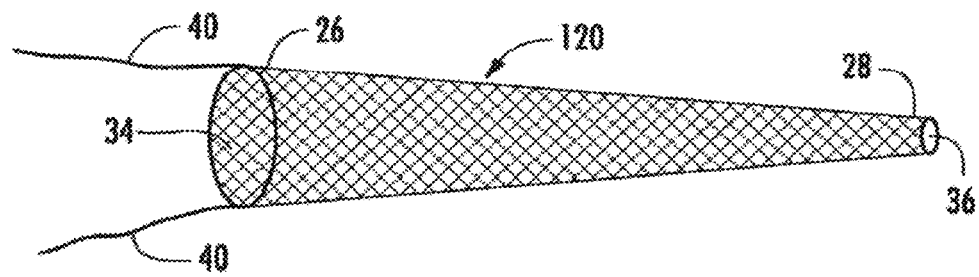
FIGS. 13-18 are perspective views showing alternate configurations for protective devices.
Figure 14:
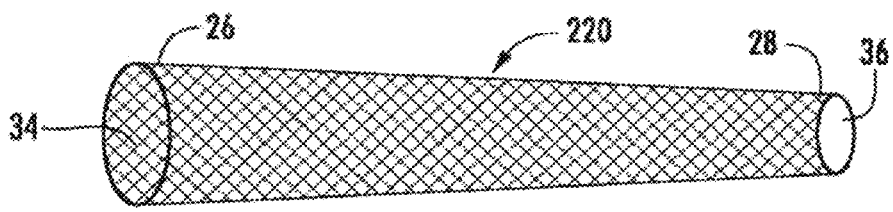
Figure 15:
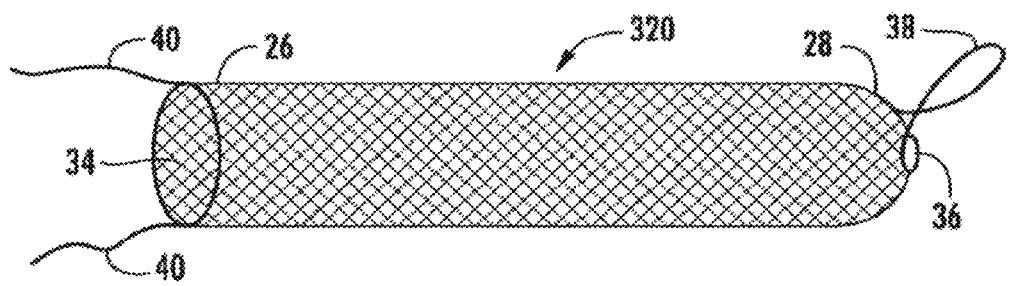
Figure 16:
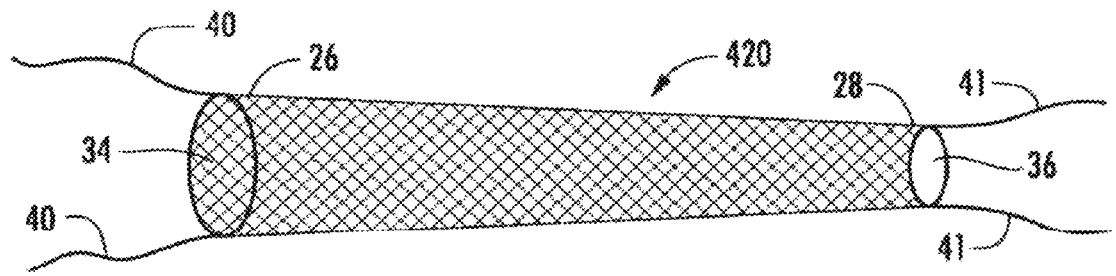

Alternate sleeve designs are shown in FIGS. 13-18. The alternate designs may be similar to sleeve 20, except for the differences noted below. For example, sleeve 120 in FIG. 13 is similar to sleeve 20, but does not include an eyelet. Sleeve 220 in FIG. 14 further excludes the threads 40 of sleeve 20. Sleeve 320 in FIG. 15 is substantially of constant diameter from first end 26 to second end 28 and only has taper near the second end. Sleeve 420 in FIG. 16 replaces eyelet 38 of sleeve 20 with additional threads 41 at second end 28.

Figure 17:
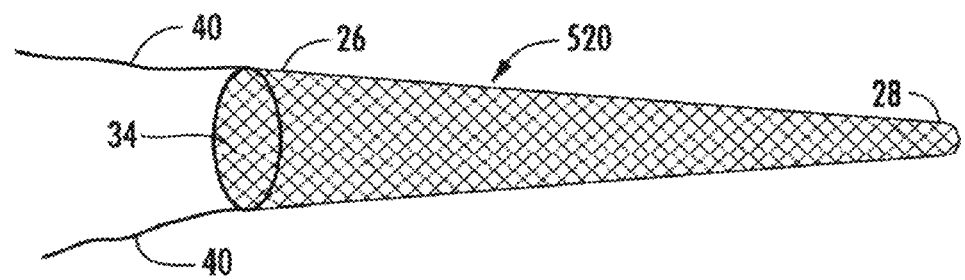

Sleeve 520 in FIG. 17 does not include the opening 36 found in second end 28 of sleeve 20.

Figure 18:
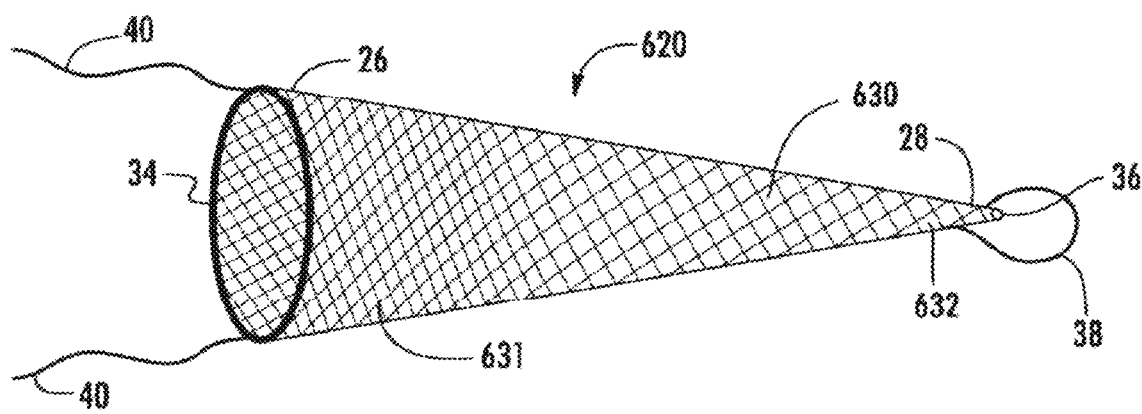

Sleeve 620 in FIG. 18 has a relatively denser mesh at portion 631 extending from first end 26 and a relatively less dense mesh at portion 632 extending from second end 28. The first portion 631 may be of lesser length (between 26 and 28) then the second portion 632. If so, first portion 631 may have a ratio of 1:2, 1:3, 1:4, etc. relative to the second portion. Alternatively, first portion 631 may have a given length (e.g. 5 mm, 10 mm, etc.) and second portion 632 may comprise the rest of sleeve 620. The denser mesh provides more protection in the area around the edge of passage 44 along the cortex portion 50. The less dense mesh provides more area for contract between tissue 22 and the bone to promote healing and attachment.

A kit may be provided including one or more sleeves 20-620 of one or more sizes, one or more tools 60, and one or more securing members such as screws and/or button connectors. Sleeves may be provided in different diameters, for example such as 3, 5, and 7 mm, with different lengths for example such as 10, 15, 20, 25 and 30 mm, to provide a surgeon with options during surgery.

Another alternate sleeve 720, as shown in FIGS. 19-31 includes a woven hollow-bore, double-tubular structure 721 and a suture portion 722. Double-tubular structure 721 includes an inner tubular structure 721*a* extending from suture portion 722 to a reversing bend 723 at an end 726 of sleeve 720 opposite an end 728 including suture portion 722. Double-tubular structure 721 also includes an outer tubular structure 721*b* extending from reversing bend 723, circumferentially around and along inner tubular structure 721*a*, and back to suture portion 722. Suture portion 722 and double-tubular structure 721 are all formed from woven strands of material (e.g., monofilament, braided monofilament, etc.), as will be discussed below.

End 726 has an opening 734 for receipt and securement of the fibrous connective tissue therein, in a similar fashion to the embodiments noted above. At least one tightening member 731 is located proximate or within end 726, as illustrated partially between inner and outer tubular structures 721*a*, 721*b*, for assisting with the securing of sleeve 720 to the fibrous connective tissue during a surgical procedure. As shown, tightening member 731 includes a tightenable loop 739 located between inner and outer tubular structures 721*a*, 721*b* and at least one extending suture portion 740 extending through outer tubular structure 721*b* for manipulation by a surgeon during a surgical procedure. Although loop 739 is shown as being located between tubular structures 721*a* and 721*b* and such provides certain manufacturing advantages (described below), it would be possible as an alternative to have loop 739 woven within either of the tubular structures 721*a*,721*b*, or substantially or fully external to outer tubular structure 721*b*.

Tightening member 731 is illustrated herein schematically, and can have one of several configurations. One possible tightening member 731 design suitable for use in sleeve 720 includes a single strand of suture material (monofilament or woven multifilament) beginning at the distal tip of one portion 740, extending through outer tubular structure 721*b* to loop 739, circumferentially around inner tubular structure 721*a* to form loop 739, and then extending through outer tubular structure 721*b* to the distal tip of other portion 740. Loop 739 may include one, two, or more circumferential courses around inner tubular structure 721*a*. Tightening member 731 utilizing such structure could also be made of more than one strand of suture material. A simple half-hitch may be used at a transition point 739*a* where suture portions 740 meet loop 739 to allow for loop 739 to remain in place until surgical use and to allow for tightening by pulling on suture portions 740 during surgical use.

However, other forms of tightening members with one or more transition points, suture portions, one or more loops, and differing knots, slip-knots, loops, nooses, etc., are possible. Tightening member 731 may thus be a strand placed within, around or over a portion of double-tubular structure 721 to form loop 739 thereon, or a pre-manufactured loop, noose, lasso, or the like, tied, looped, and/or pierced, for sliding in a direction to tighten and close loop 739 when suture portion(s) are pulled.

Figure 19:
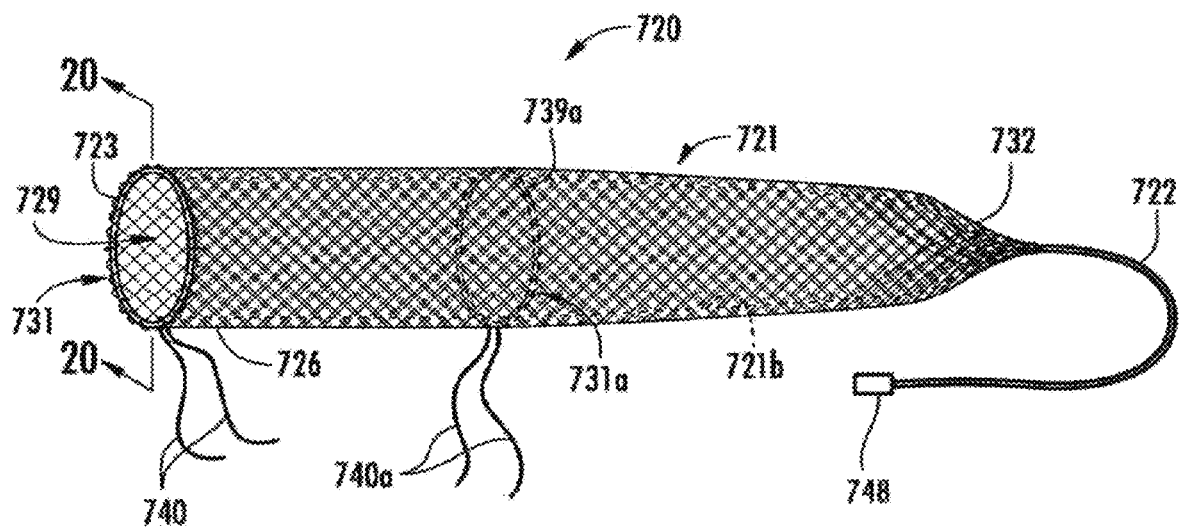
FIG. 19 is a perspective diagrammatic view of another alternate configuration for a protective device.
Figure 20:
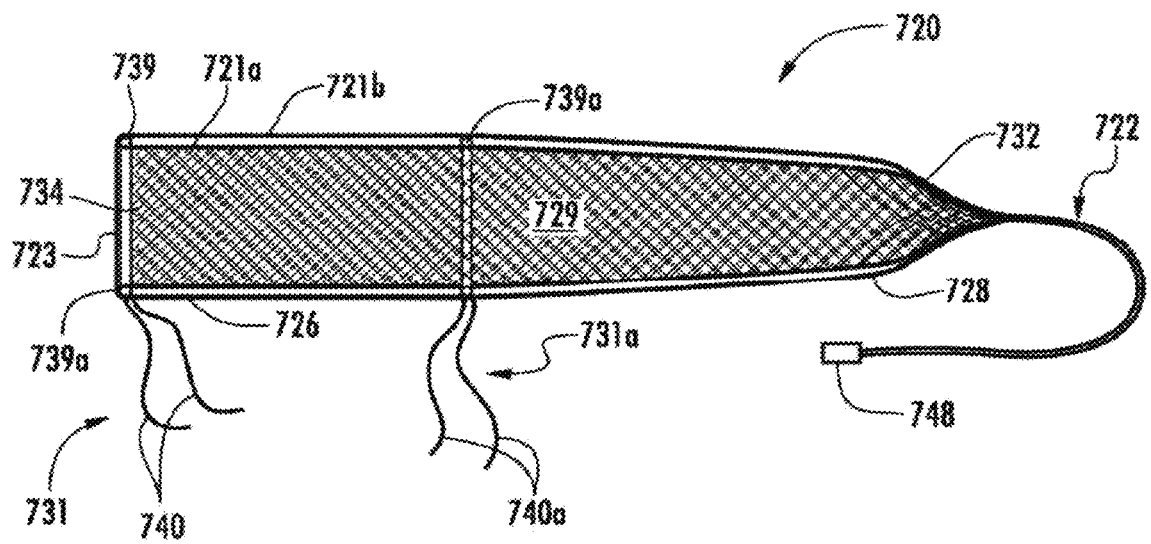
FIG. 20 is a cross-sectional view through the protective device of FIG. 19.

In the deployment-ready configuration of FIGS. 19 and 20, sleeve 720 defines a passage 729 sized for receiving the fibrous connective tissue therein during a surgical procedure (see FIGS. 26-29). Passage 729 extends from circumferential reversing bend 723 at end 726 toward end 728 and terminates at suture portion 722.

Tightening member 731 is thus movable between a first loosened position (see FIGS. 28-29) in which passage 729 at circumferential reversing bend 723 is sized sufficiently for receipt of the fibrous connective tissue into the passage and a second tightened position (see FIG. 30) in which the passage at the circumferential reversing bend is reduced in size sufficiently to assist in securing the fibrous connective tissue in place in sleeve 720. Tightening member 731 may include external texture or small frictional features as noted above so as to provide a self-locking function wherein, once moved to the second position the tightening member 731 opposes movement back toward the first position and/or holds the tightening member in place on the tissue.

If desired, at least one additional tightening member may be provided along or within sleeve 720. As shown, member 731*a* is spaced from tightening member 731 in a direction along sleeve 720 toward second end 728. It should be understood that the one or more additional tightening members may be located in other positions along sleeve 720 than those shown. Also, it should be understood that sutures 740, 740*a* extending from one or all tightening members may be used as described above (see FIG. 31) to stitch, whipstitch, etc., sleeve 720 to the fibrous connective tissue to assist in creating a surgical construct ready for implantation.

The double-tubular structure 721 may have a strand weave density sufficient to allow tissue growth between the strands after securement to the bone. The strand weave density may vary between circumferential reversing bend 723 and suture portion 722. In particular, the strand weave density may be higher in a neck-down portion 732 adjacent suture portion 722 than along other portions of double-tubular structure 721. It can thus be said that inner tubular structure 721 defines an inner diameter along passage 729 that decreases in neck-down portion 732 in a direction toward suture portion 722.

In the example shown, sleeve 720 is may be woven in many formats depending on desired use. For example, the number of strands woven could be 12, 24, 36, etc., depending desired on size, desired strand density for strength or tissue growth, etc. Strands may be made for example of ultra-high molecular weight polyethylene (UHMEPE), polypropylene, polyester, or other materials. Strands may be coated with materials or surface treated for promoting tissue healing, bone growth, reduced friction (PTFE) etc. Strands or portions may be non-absorbable or bio-resorbable. Strands may each be monofilament or may be braided from multiple filaments. A size 5-0 USP (size 1 Metric) monofilament strand available, for example under the brand name Force Fiber® from Teleflex, Inc. is one example of a strand that may be used. Such strand has a nominal diameter of about 4 mils to about 6 mils, although larger sizes could also be used. If larger (stronger) strands are used, fewer strands may be required. A mix of larger and smaller strands and/or braided and monofilament strands may also be used to provide different characteristics to the resulting sleeve (e.g., linear pull strength vs. self-locking grip around tissue or other aspects). The strand number and choice, and size and shape of the resulting sleeve will be dictated by the application (e.g., hand surgery, shoulder surgery, hamstring surgery, ACL surgery; child or adult patient; type of connection to bone or tissue—screw in tunnel, button or other).

For example, for a tendon surgery on a child, passage within double-tubular structure portion 721 of sleeve may have an inner diameter of about 4 mm and a length of about 20 mm. For a hamstring or ACL surgery on an adult, the inner diameter may be about 10-12 mm and length about 35 mm. The suture portion 722 can have differing lengths a well, mostly depending on how it will be manipulated and secured during surgery. Suture portion 722 may thus have a length of only a few inches, but may be about 25 cm (about 10 inches) to about 75 cm (about 30 inches in some applications). Suture portion 722 may be used to pull the sleeve 720 and tissue 22 construct through and into place, to anchor the construct in place via a screw, button or the like, etc. Once anchored for example in a bone tunnel by a screw, a distal end of suture portion 722 may be used as an internal brace for further surgical connection. End treatment 748 of suture portion 722 can include a wax, a heat block weld, etc., to prevent fraying and to allow threading of suture portion into an eyelet or into or through a body cavity or medical device.

Tightening members can be made of various designs as well. Such strands may be woven or braided of several filaments, and may be thicker and stronger than some or all of the individual strands (mono or multifilament) woven into double-tubular structure 721. Tightening members may be made of the above materials or others. Tightening members may have strand size larger than 5-0, whether monofilament or multifilament, and may have mixtures of sizes. Portions 740 may function as sutures for stitching through tissue 22 to assist in securing the tissue to sleeve 720.

It should be understood that the above parameters are exemplary only, and that differing configurations and sizes of portions of sleeve 720 can be implemented in view of the surgical application contemplated. Thus, different numbers of strands, strands of differing types and/or diameters also be used to provide differing characteristics (e.g., tensile strength, texture/grip/self-locking function, coatings, medications, loops, suturing strands, etc.) useful to the resulting sleeve, for example in terms of connection to the fibrous connective tissue, contact with bone, connection to buttons or screws, etc.

Figure 24:
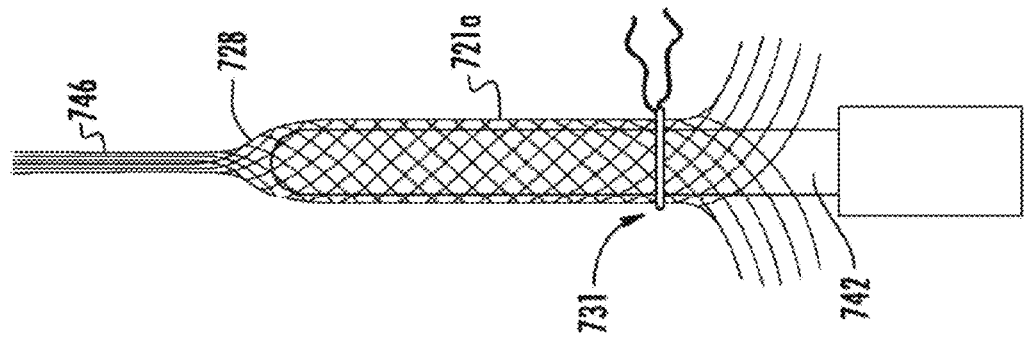
FIGS. 21-27 are perspective diagrammatic views showing sequential steps in one possible manufacturing process for the protective device of FIG. 19.
Figure 23:
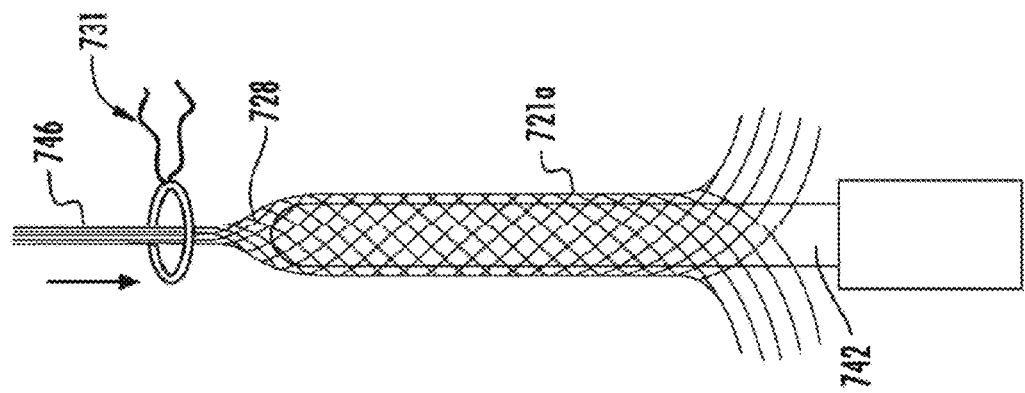
Figure 22:
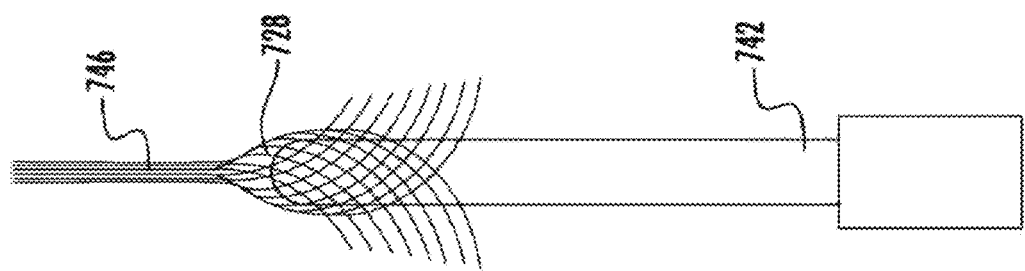
Figure 21:
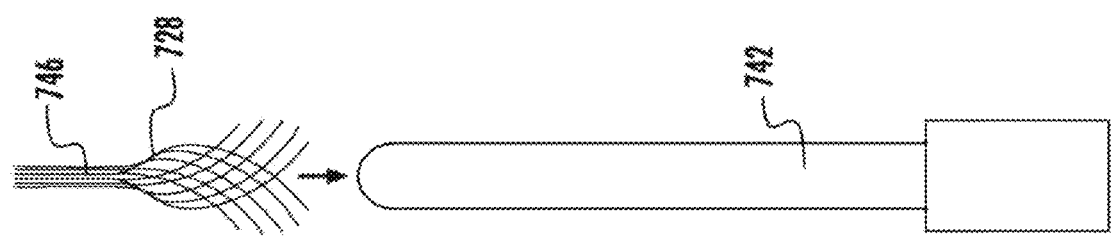
Figure 27:
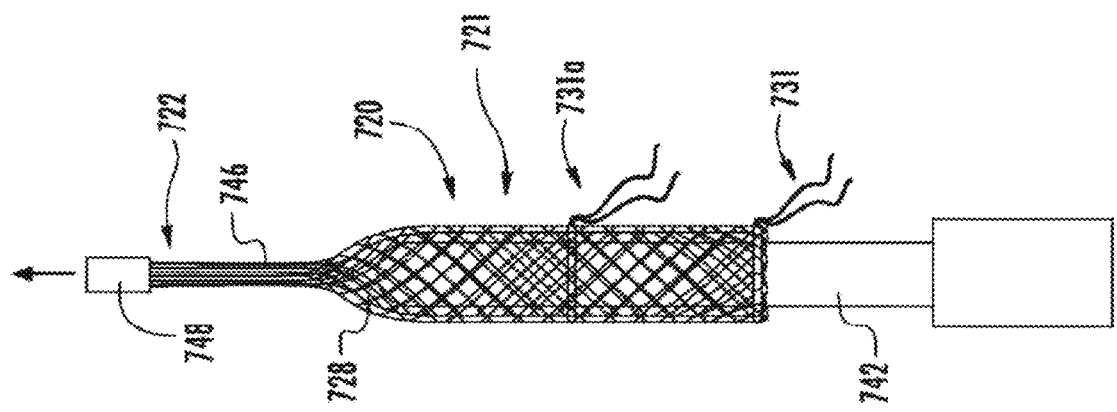
Figure 26:
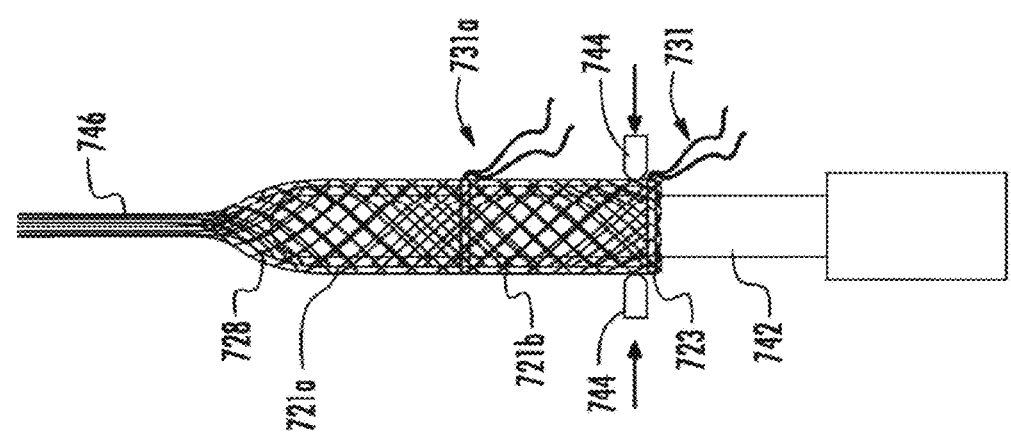
Figure 25:
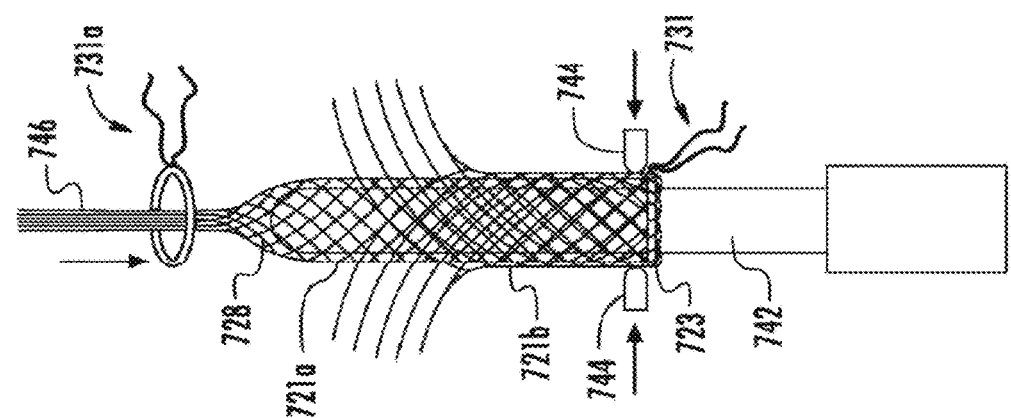

To weave a sleeve such as sleeve 720, a plurality of strands may be employed in a circular weaving device, with distal ends of the threads forming part of suture portion 722, which may employ loose strands, tightly woven strands, or tightly twisted strands. The weave begins to widen at necking-down portion 732 and may continue over an arbor, mandrel or the like (742) to define a desired diameter (see FIGS. 21 and 22). As weaving continues from second end 728 and toward first end 726 (i.e., the second end as defined above is woven before the first end). The part of double-tubular structure 721 being woven to this point is the inner tubular structure 721a. Once the weaving process gets to a desired length, a tightening member 731 can be placed and/or woven in along the sleeve at a point between the first end and the second end (FIGS. 23 and 24). As shown, a pre-manufactured tightening member 731 can be slid downward so that loop 739 is in a desired location (vertically, as shown), although an alternate tightening member could be applied horizontally, for example with loop 739 being formed in place. After placing tightening member 731, the weave direction is reversed, holders 744 can be employed, and weaving continues (FIGS. 25 and 26). One or more additional tightening member(s) 731a can be added along the way if desired. The reversing of the weave forms a circumferential reversing bend 723, and further weaving creates the outer tubular structure 721b. Weaving may overlap some strands between inner and outer tubular structures, for example to secure tightening member(s) in place or to connect the tubular structures; however, the tubular structures may remain separate along their lengths. After necking-down portion 732 is passed again, trailing distal ends of the woven strands form an extending part 746 of suture portion 722 (FIG. 26). Before or after removal of sleeve 720 from arbor 742, an end treatment 748 (FIG. 27) may be applied to the tip of extending part 746, in the form of a wax or plastic cover, heat block weld, clip, knot, etc., to keep the strands together and prevent unraveling of sleeve 720. End treatment 748 may also include some or all of surgically useful elements, such as a button structure, loop, or the like as noted above, which may be attached at manufacturing or during surgery.

In surgical use sleeve 720 is similar to those described above, as shown in FIGS. 28-31. Sleeve 720 is first slipped over the fibrous connective tissue 22 (FIGS. 28 and 29). The weave of sleeve 720 may be loose enough to manipulate, so if desired a thin grasping tool such as a forceps, a lasso suture, etc. (not shown) may be inserted through the weave along passage 729 toward second end 728 and extending toward or though opening 734 to grasp tissue 722 and pull it into the passage. The weave of sleeve 720 may due to its tubular narrowing, structure tighten and self-lock (akin to a "finger trap") due to extension of sleeve during insertion of the tissue. After insertion, any tightening member(s) 731, 731a present may be tightened by pulling taut threads 740,740a (FIG. 30), thereby closing loops 739 tightly around tissue 22 to at least assist with holding sleeve 720 in place. Threads 740,740a may then be stitched into the construct, knotted, clipped off, etc., as desired to further secure sleeve 720 around the tissue and/or remove extraneous suture material as needed (FIG. 31). Sleeve 720 may thereafter be surgically introduced and secured in the body in various ways, and suture portion 722 may be utilized in various ways as discussed above.

FIG. 32 shows an example of an alternate device and kit including an introducer, and FIGS. 33-40 show one possible surgical method using the device and kit of FIG. 32. FIGS. 32-40 are highly schematic for clarity, and FIGS. 19-31 should be consulted to see more details of commonly included elements.

As shown in FIGS. 32-40, sleeve 720 includes woven, reversing threads defining passage 729 (as described above), suture portion 722 at a closed end D, and the open end C a "lasso" shaped tightening member 731, including a loop 739 surrounded by the weave and threads 740 extending from the weave. Fibrous connective tissue 22 is also as described above, although a passing suture E is attached to one end of the connective tissue 22 via stitching K. An optional frictional holding stitch L (described below) may be spaced from the end with the passing suture E. The passing suture E is employed with a passing needle J having an eyelet F for receiving the passing suture at one end and a sharp tip G at the other end.

Introducer 760 is a generally tube-shaped element having an outer diameter just smaller than that of passage 729 within sleeve 720. During manufacture, introducer 760 may be put in place on arbor 742 (see previous figures) before weaving, or the introducer may be inserted during or after weaving. Introducer 760 may have a smooth (low frictional) outer surface texture to allow the introducer to slide freely within sleeve 720, or it may have a continuous or discontinuous a surface texturing that also assists in frictionally holding the threads in place about the introducer during weaving or during surgical use.

If desired, introducer 760 may have a lengthwise slit 762 running all or part of the way between open ends A and B to allow for radial flex during insertion of the connective tissue 22 and/or during removal of the introducer 760 after insertion of the connective tissue. Slit 762 may have edges with some circumferential overlap (as shown), or may have butted edges with no overlap, or spaced edges with no overlap.

Introducer 760 may have a relatively smooth internal surface that connective tissue 22 may readily slide through. Use of introducer 760 may help prevent connective tissue 22 from snagging threads when being inserted into sleeve 720 by guiding the connective tissue into place, as described below, without friction that could deform sleeve 720, or snag or damage connective tissue 22 or any of its connected sutures. Introducer 760 may also have a feature configured for assisting in grabbing and removing it from sleeve 720, such as a tab 764, or a non-protruding opening, slot, etc. for receipt of or interaction with a tool such as a forceps or other surgical tool (not shown).

One method of use of sleeve 720 with introducer 760 will be described with reference to FIGS. 33-40. It should be understood that other methods are possible, depending on the application, sizes of elements needed, type of surgery, etc.

As shown in FIG. 33, a sleeve 720/introducer 760 assembly is readied for surgical use. As shown, introducer 760 is within passage 729, end B of introducer is near closed end D of sleeve 720, and end A of introducer 760 is near and extends from open end C of sleeve 720.

As shown in FIG. 34, connective tissue 22 has been prepared with passing suture E attached, if desired by placing a suture K such as a simple luggage tag style suture or other, into the connective tissue end. Optional Holding stitch L may also be applied to connective tissue 722 at a distance from the suture K end that will ensure that stitch L remains within passage 729 after insertion and tightening of sleeve 720 around connective tissue. In particular, stitch L should be located so as to be near and internal to loop 739, as discussed below. Free end of passing suture E is placed into eyelet F of passing needle J.

Figure 35:
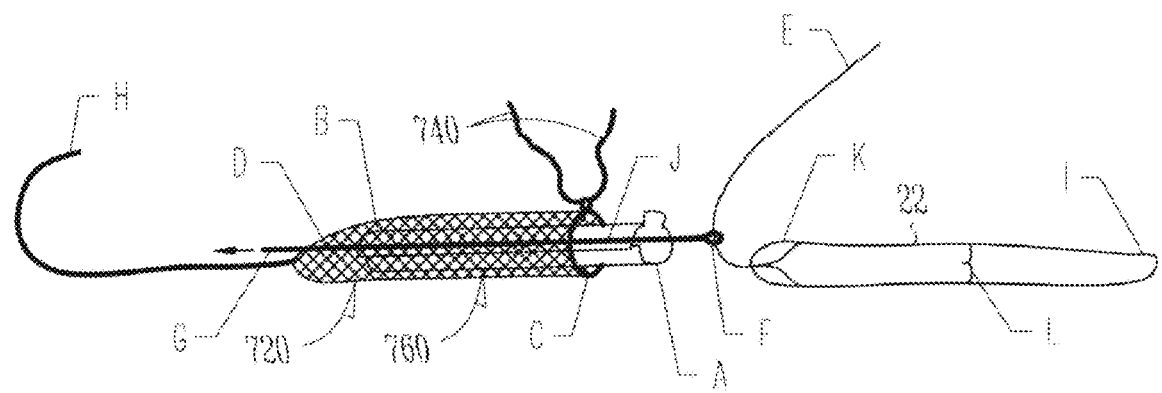

In FIG. 35, passing needle J is delivered through into open end A of introducer 760 and therefore into open end C of sleeve 720 until sharp tip G extends out of end B of introducer and pierces the weave of closed end D of sleeve 720.

Figure 36:
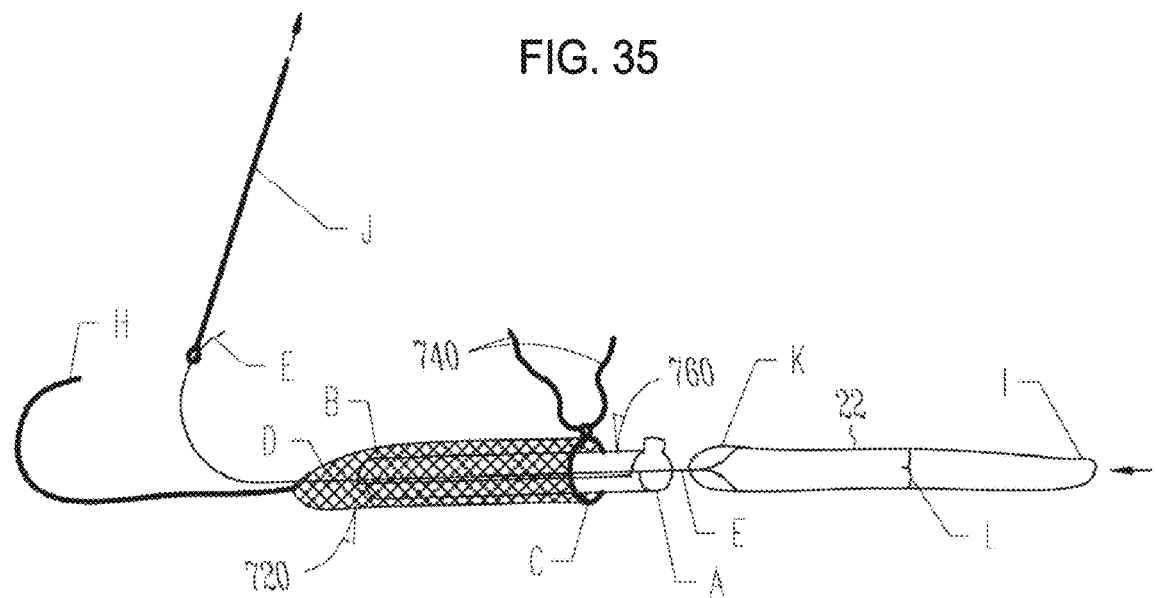

If FIG. 36, passing needle J has been pulled completely though closed end D of sleeve 720 so that passing suture is pulled though and extends through closed end D through the weave there, longitudinally through introducer 760, and out open ends A and C to connective tissue 22. Passing suture E should be made long enough to permit such manipulation.

Figure 37:
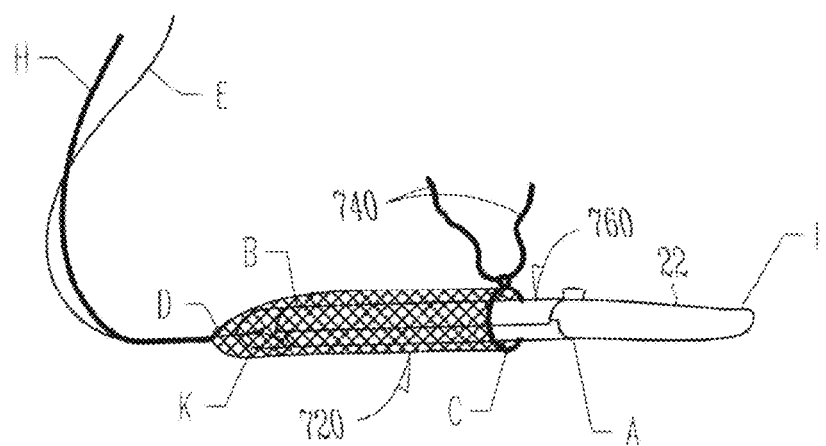

In FIG. 37, passing suture E is further to draw the connective tissue into and partially through introducer 760 while grasping end c of sleeve 760 to prevent slippage of sleeve toward end B of introduced while pulling passing suture E. The end of connective tissue 22 with suture K may thus extend from end B of introducer 760 and will through contact with closed end D stretch sleeve 720 longitudinally, while also beginning to radially tighten sleeve 720 with the self-locking function noted above. Note that the distance between ends C and D has increased due to this pulling and the resulting reconfiguring of sleeve 720.

Figure 38:
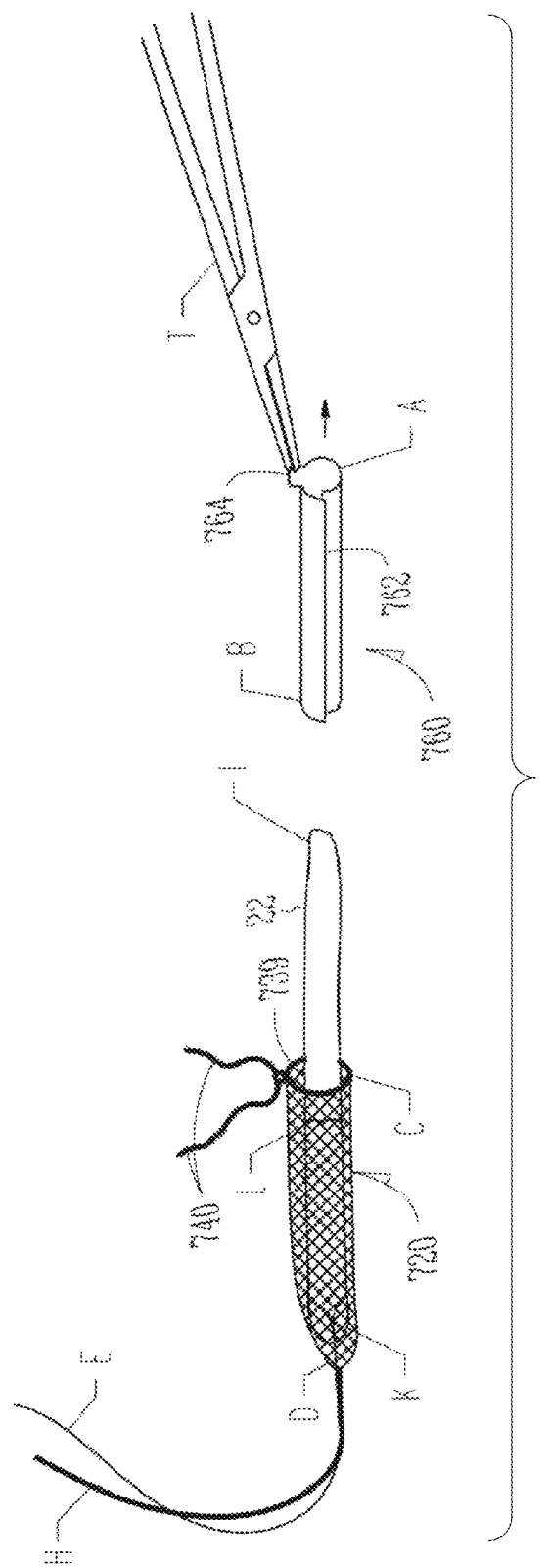

FIG. 38 shows removal of introducer 760 by grasping it with a simple clamp T at end A (or by its handle/tab/opening structure 764, if present) and pulling it out of passage 729 of sleeve 720 while also holding passing suture E, suture H, and/or sleeve end D, etc. Introducer 760 thus slides out of sleeve 720 without disrupting the sleeve weave or dislodging connective tissue 22 from its place within passage 729. Introducer 760 and passing needle J may then be discarded.

Figure 39:
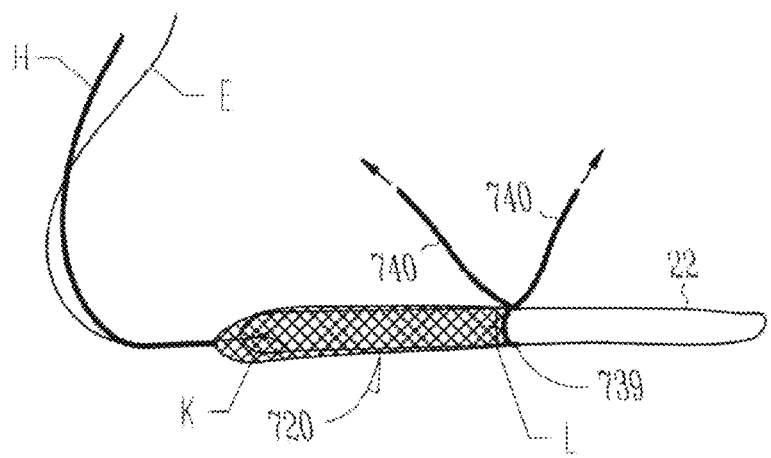

In FIG. 39, the lasso loop 739 is tightened around connective tissue 22 by pulling on sutures 740. If desired, suture ends 740 can be sewn into the connective tissue and/or passed around the connective tissue to form an additional loop, tied and or stitched, according to surgeon's preference. Note that stitches L are still within sleeve 720 near tightened loop 739.

Figure 40:
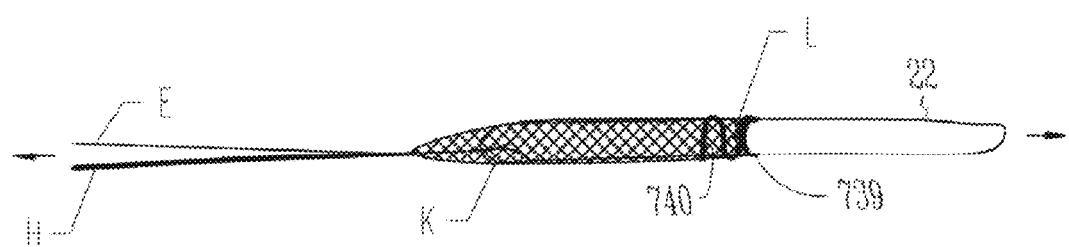

In FIG. 40, with the connective tissue 22 secured in the sleeve 720 and locked in place with the lasso loop 739, suture 740, etc., suture H can be pulled one direction (to the left as depicted) while connective tissue end I be pulled in the opposite direction (right as depicted) to thus further lock the connective tissue within the sleeve. Suture H and E if not removed or stitched in earlier) can thus be stitched in place, used to form a loop for receipt of a screw, button, etc., used to mount other attachment structure, etc., depending on the surgical application. Stitch L assists in holding connective tissue 22 in place during the tightening and afterward, by providing additional frictional resistance opposing slippage of the connective tissue out of sleeve when the construct is placed in tension. Placing stitch L interior to loop 739 enhances such frictional opposition to relative sliding movement, especially after the tightening of loop 739. Such pulling of the ends can also be considered "pre-tensioning" the device. The construct can then be secured to bone by surgeon's preference.

Sleeve 720 may be woven from multiple threads of 4.0 sized ultra-high molecular weight polyethylene (UHMWPE) threads, such as FiberWire® sutures available from Arthrex, Inc. 12 threads may be used, but other numbers such as 8 or 16 could also be used. The number and arrangement of such threads may vary dependent on the application (distal extremity vs large joint surgeries). In some surgical applications, for example where the construct is installed in a tunnel held in place by a button attached to sutures such as suture H, it may be more important to have high ultimate tensile strength ratings for the construct, such as over 250N, or more particularly at least or over 400N. In other applications (for example where a Tenodesis® screw holds the construct in a socket) such high tensile strength might not be as important.

Accordingly, a device, a kit, a method of manufacturing, and a surgical method are disclosed in which a sleeve is used to protect a distal end of a fibrous connective tissue. Use of a reversing bend provides a stronger, overlapping structure as compared to no reversing bend. Use of the tightening members also provides a stronger structure. Use of the tightening members and circumferential revering bends provides a synergy useful in some applications. Use of an introducer assists in placing the connective tissue reliably in the sleeve where desired without snagging, deforming, etc. While preferred embodiments of the invention have been described above, it is to be understood that any and all equivalent realizations of the present invention are included within the scope and spirit thereof. Thus, the embodiments depicted are presented by way of example only and are not intended as limitations upon the present invention. Thus, while particular embodiments of the invention have been described and shown, it will be understood by those of ordinary skill in this art that the present invention is not limited thereto since many modifications can be made. Therefore, it is contemplated that any and all such embodiments are included in the present invention as may fall within the literal or equivalent scope of the appended claims.

I claim:

1. A protective device for a fibrous connective tissue to be secured within a passage in a bone by a securing device, the protective device comprising:
    a sleeve woven from a plurality of strands, the sleeve having a double-tubular structure and a suture portion, the double-tubular structure having an inner tubular structure and an outer tubular structure circumferentially surrounding the inner tubular structure, the strands extending from respective first ends through the suture portion, through the inner tubular structure, reversing direction at a circumferential reversing bend, through the outer tubular structure, and through the suture portion to respective second ends, an opening defined at the circumferential reversing bend and a passage extending from the opening toward the suture portion within the double-tubular structure, the opening and passage being sized for receipt and securement of the fibrous connective tissue therein; and
    a tightening member located along the sleeve proximate the circumferential reversing bend, the tightening member including a loop movable between a first loosened position in which the loop is sized sufficiently to permit movement of the fibrous connective tissue therethrough into the passage and a second tightened position in which the loop is reduced in size sufficiently to assist in securing the fibrous connective tissue in place in the passage.

2. The protective device of claim 1, wherein the loop is woven into the double-tubular structure.

3. The protective device of claim 2, wherein the loop is located between the inner tubular structure and the outer tubular structure.

4. The protective device of claim 2, wherein the tightening member further includes at least one strand extending from the loop through the outer tubular structure.

5. The protective device of claim 1, wherein the tightening member includes an external frictional structure for resisting movement from the second tightened position toward the first loosened position.

6. The protective device of claim 1, further including at least one additional tightening member including a loop and spaced from the tightening member in a direction along the double-tubular structure toward the suture portion.

7. The protective device of claim 6, wherein the at least one additional tightening member is movable between a first loosened position and a second tightened position.

8. The protective device of claim 1, wherein the double-tubular structure has a strand weave density sufficient to allow tissue growth between the strands after securement in the bone.

9. The protective device of claim 8, wherein the strand weave density varies between the circumferential reversing bend and the suture portion.

10. The protective device of claim 9, wherein the strand weave density is higher in a neck-down portion adjacent the suture portion than along other portions of the double-tubular structure.

11. The protective device of claim 10, wherein the inner tubular structure defines an inner diameter along the passage, the inner diameter decreasing in the neck-down portion in a direction toward the suture portion.

12. The protective device of claim 1, wherein the double-tubular portion is configured to move from a rest position to a self-lockingly tightened position when the fibrous connective tissue is inserted into the passage and the double-tubular structure is stretched in a direction along the passage.

13. The protective device of claim 12, wherein at least a portion of the strands have an external frictional structure for resisting movement from the self-lockingly tightened position toward the rest position.

14. A surgical method of securing a fibrous connective tissue having a distal end portion within a passage in a bone, the surgical method comprising:
    inserting the distal end portion of the fibrous connective tissue into a passage within a protective device having:
    a sleeve woven from a plurality of strands, the sleeve having a double-tubular structure and a suture portion, the double-tubular structure having an inner tubular structure and an outer tubular structure circumferentially surrounding the inner tubular structure, the strands extending from respective first ends through the suture portion, through the inner tubular structure, reversing direction at a circumferential reversing bend, through the outer tubular structure, and through the suture portion to respective second ends, an opening defined at the circumferential reversing bend and a passage extending from the opening toward the suture portion within the double-tubular structure, the opening and passage being sized for receipt and securement of the fibrous connective tissue therein; and
    a tightening member located along the sleeve proximate the circumferential reversing bend, the tightening member including a loop movable between a first loosened position in which the loop is sized sufficiently to permit movement of the fibrous connective tissue therethrough into the passage and a second tightened position in which the loop is reduced in size sufficiently to assist in securing the fibrous connective tissue in place in the passage;
    placing the distal end portion into the passage into the sleeve;
    securing the fibrous connective tissue within the passage in the sleeve at least partially by tightening the loop;
    inserting the fibrous connective tissue and protective device at least partially into the passage in the bone; and
    securing the fibrous connective tissue and protective device to the passage in the bone.

15. A method of manufacturing a protective device configured for securing a fibrous connective tissue therein for use during surgery, the method comprising:
    forming a sleeve having a double-tubular structure from a plurality of plurality of strands by weaving from respective first ends, through a suture section, through an inner tubular structure, reversing at a circumferential reversing bend, through an outer tubular structure, through the suture portion to respective second ends, an opening defined at the circumferential reversing bend and a passage extending from the opening toward the suture portion within the double-tubular structure, the opening and passage being sized for receipt and securement of the fibrous connective tissue therein; and placing a tightening member along the sleeve proximate the circumferential reversing bend, the tightening member including a loop movable between a first loosened position in which the loop is sized sufficiently to permit movement of the fibrous connective tissue therethrough into the passage and a second tightened position in which the loop is reduced in size sufficiently to assist in securing the fibrous connective tissue in place in the passage.

16. The method of claim 15, further including weaving at least one additional tightening member spaced from the tightening member in a direction along the sleeve toward the suture portion.

17. The method of claim 15, wherein double-tubular structure woven with a strand weave density which varies between the circumferential reversing bend and the suture portion.

18. The protective device of claim 1, further including a removable introducer having a generally tubular shape sized for placement through the opening into the passage for guiding the fibrous connective tissue into the passage, wherein the removable introducer includes a slit extending axially along the introducer.

19. The protective device of claim 18, wherein the introducer has a protruding gripping portion located at an end of the introducer adjacent the opening for assisting in removing the introducer but not the fibrous connective tissue from the passage.

20. The surgical method of claim 14, wherein the step of inserting the distal end portion of the fibrous connective tissue into the passage within the protective device includes inserting the distal end portion of a generally tubular introducer into a passage within a protective device;

inserting the fibrous connective tissue distal end portion into the introducer; and removing the introducer but not the fibrous connective tissue distal end portion from the a passage within the sleeve.

* * * * *